United States Patent [19]

Pharriss et al.

[11] 4,014,988
[45] Mar. 29, 1977

[54] METHOD FOR TREATING HYPERMENORRHEA WITH UTERINE THERAPEUTIC SYSTEM

[75] Inventors: Bruce B. Pharriss, Palo Alto; Ross R. Erickson, Sunnyvale; Stephen A. Tillson, Los Altos, all of Calif.

[73] Assignee: Alza Corporation, Palo Alto, Calif.

[22] Filed: Oct. 31, 1975

[21] Appl. No.: 627,506

[52] U.S. Cl. .............................. 424/14; 424/241; 424/242; 424/243

[51] Int. Cl.² .................. A61K 9/02; A61K 31/58; A61K 31/56

[58] Field of Search ............ 424/242, 243, 14, 282, 424/241

[56] References Cited

OTHER PUBLICATIONS

Cumulated Index Medicus, vol. 14 (1973) p. 6734.
Modern Drug Encyclo., 12th edit. (1973) p. 644.

*Primary Examiner*—Sam Rosen
*Attorney, Agent, or Firm*—Paul L. Sabatine; Thomas E. Ciotti; Edward L. Mandell

[57] ABSTRACT

A method for treating hypermenorrhea is disclosed. The method comprises continuously administering controlled low dosage amounts of a progestational hormone to the uterus to impart relief from hypermenorrhea.

17 Claims, 7 Drawing Figures

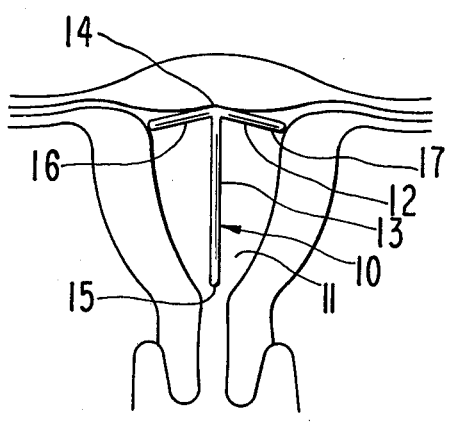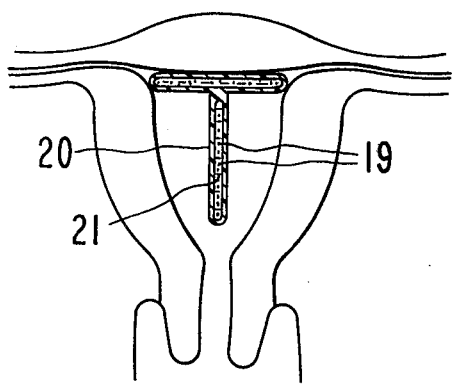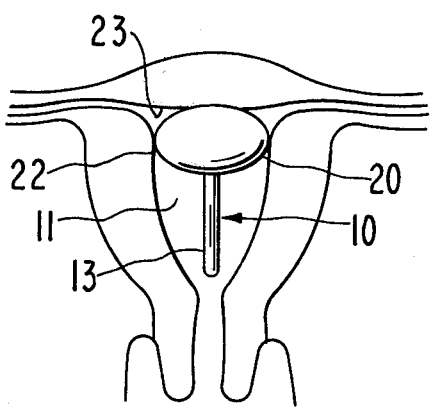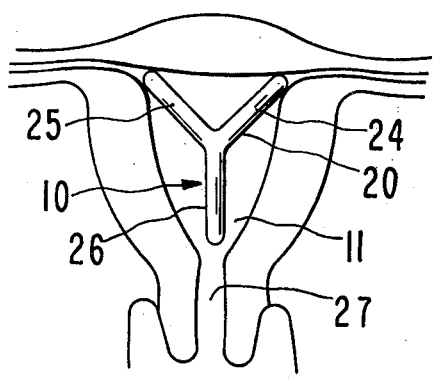

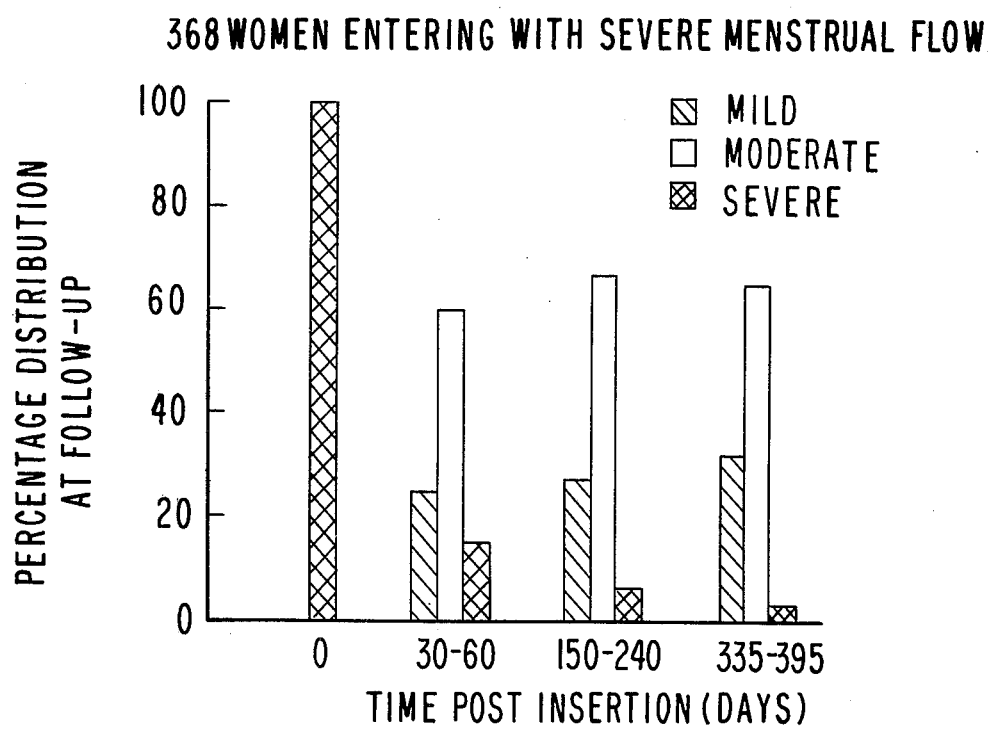

METHOD FOR TREATING HYPERMENORRHEA WITH UTERINE THERAPEUTIC SYSTEM

BACKGROUND OF THE INVENTION

1. Field of the Invention

This invention pertains to gynecologic pharmacology. More particularly, the invention relates to a method for the management of hypermenorrhea in warm blooded animals by continuously administering a progestational hormone in a therapeutically effective amount to the uterus of an animal having hypermenorrhea.

2. Description of the Prior Art

Hypermenorrhea is clinically excessive uterine bleeding occurring at regular intervals with the period of flow being of usual duration. *Illustrated Medical Dictionary*, by Dorland, 24th Edition, page 704, 1971, published by W. B. Saunders Company, Philadelphia, Penna. It is the most common disorder of menstrual function that occurs during the reproductive life. *Gynecologic Endocrinology*, Edited by Gold, J. J., Chapter 14, by Scommegna, A., page 349, 1968, published by Harper & Rowe, New York. At present, hypermenorrhea is treated by parentral administration of progesterone or by oral administration of progestins. However, several disadvantages are associated with these modes of treatment that severely restrict their medical use. For example, parenteral administration requires successive injections and after the last injection withdrawal bleeding ensues. This method is unsuited for many patients because they cannot stand the pain of injection and the anticipation of a return to bleeding. The oral method is unsuited for many patients because they cannot tolerate oral medication and the benefits obtained usually cease when the patient stops the treatment. See Scommegna, A., as cited supra at page 351. The prior art has administered low doses of progesterone over a prolonged period of time locally to the uterus for fertility control, but it has not administered progestational steroids directly to the uterus for the management of hypermenorrhea. Scommegna, A., *Obst. and Gynec.*, Vol. 43, No. 5, pages 769 to 779, 1974 and British Pat. No. 1,318,554. In view of the above presentation, it becomes immediately apparent that a critical need exists for a method useful for the management of hypermenorrhea and if such a method were made available, it would represent a valuable contribution of the useful medical arts.

OBJECTS OF THE INVENTION

Accordingly, it becomes an immediate object of this invention to provide a new and useful method for the management of hypermenorrhea.

Still hormonal object of the invention is to provide a method for treating a female suffering with hypermenorrhea comprising releasing in the female's uterine cavity a therapeutically effective amount of at least one progestational hormal steroid to relieve the excessive bleeding associated with hypermenorrhea.

Yet another of object of the invention is to provide a method for treating hypermenorrhea comprising administering a progestational steroid to the uterine endometrium in low dosage amounts over an extended duration of time for substantially reducing hypermenorrhea.

Yet still another object of the invention is to provide a method for treating hypermenorrhea comprising administering a progestational agent from an intrauterine therapeutic system in the form of an intrauterine device to the uterus for relieving hypermenorrhea.

Other objects, features and advantages of the invention will be more apparent to those skilled in the art from a reading of the present disclosure and the accompanying claims.

SUMMARY OF THE INVENTION

This invention concerns a method for the management of hypermenorrhea comprising administering a progestational steroid to the uterus in an amount needed to produce relief from hypermenorrhea. The method uses small doses of progestational steroids and achieves the effect without administering excessive amounts to the uterus and it is substantially free of systemic absorption.

Specifically, the method comprises administering progestational steroid to the uterus from an intrauterine therapeutic system in the form of an intrauterine therapeutic device in a continuous and controlled therapeutically effective low dosage amount up to 200 micrograms per hour to lessen the effects of hypermenorrhea.

BRIEF DESCRIPTION OF THE DRAWINGS

FIG. 1 is a view illustrating an intrauterine therapeutic system having a transverse member and a perpendicular member positioned in the uterus;

FIG. 2 is a cross sectional view of the intrauterine therapeutic system of FIG. 1 manufactured with a reservoir;

FIG. 3 is a sectional view of the uterine cavity showing another embodiment of an intrauterine therapeutic system properly positioned in the cavity;

FIG. 4 is a view depicting an intrauterine therapeutic system having a continuous curved shape positioned in a uterus; and FIGS. 5a, 5b and 5c represent the results obtained by practicing the method of the invention.

In the drawings and specification, like parts in related figures are identified by like numbers. The terms appearing earlier in the specification and in the description of the drawings, as well as embodiments thereof, are further described elsewhere in the disclosure.

DETAILED DESCRIPTION OF THE DRAWINGS

Figure 5A:
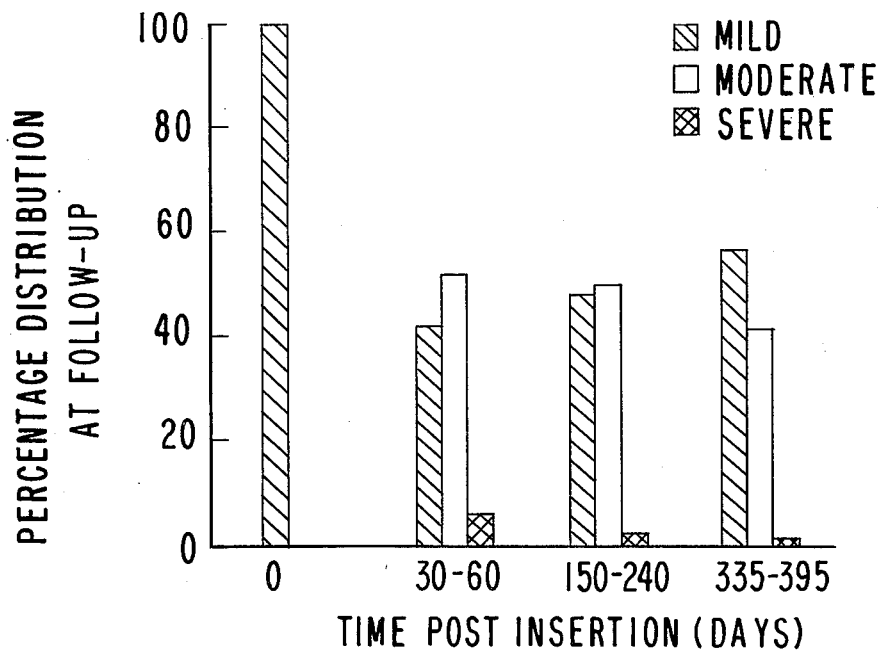

Turning now to the drawings in detail, which are examples of intrauterine therapeutic systems that can be used for releasing a progestational hormone to the uterus for the management of hypermenorrhea and which examples are not to be construed as limiting the invention, one embodiment thereof is seen in FIG. 1. The phrase "intrauterine therapeutic system" as used herein embraces as functional equivalents "intrauterine therapeutic system in the form of an intrauterine therapeutic device", "intrauterine device," and "system." In FIG. 1, a system 10 is seen positioned in uterine cavity 11. System 10 is comprised of a transverse member 12 suitably fixed to a dependent member 13. Member 12 has a lead end 14 and a distant end 15. Member 12 interconnects with dependent member 13 at front end 16 with member 14 extended outwards in two directions from member 13 to define arm 16 and arm 17, a right and left arm respectively. Arms 18 and 19 each terminate in a rounded end to prevent any possible damage to the wall of uterus 11. System 10 is substantially T-shaped and it is sized and shaped to fit all uterine cavities. Its dimensions can be made to conform to the nulliparous and multiparous uterine cavities. Generally, members 12 and 13 have a length of 20 to 40 millimeters and a diameter of 1 to 4 millimeters. System 10 for the purpose of this invention is manufactured with steroid releasing means, not shown in FIG. 1. The releasing means can comprise steroid distributed throughout the system when it is formed of a polymeric filament, or the steroid can be housed in a reservoir within the system. An intrauterine T-shaped system as disclosed above was disclosed by Tantum, H. J., in U.S. Pat. No. 3,533,406. Another intrauterine device similar to the device described above and suitable for the present purpose, is the 7-shaped device as disclosed by Abramson, H. J., in U.S. Pat. No. 3,777,748.

FIG. 2 illustrates the system of FIG. 1 in cross section manufactured with a reservoir 18 for containing a progestational agent 19. Reservoir 18 is formed by a wall 20 surrounding an internal space in members 12 or 13 and it contains a steroid 19, and a carrier 21 permeable to the passage of steroid 19. Wall 20 is formed of a steroid release rate controlling material permeable to the passage of steroid 19 but at a lower rate than through carrier 21. In operation, steroid 19 dissolved in carrier 21 is released from system 10 by diffusion through wall 20 at a rate controlled by wall 20. The system of FIG. 2 is described in U.S. Pat. No. 3,845,761.

FIG. 3 illustrates another intrauterine system 10 useful for releasing progestational steroids to uterus 11 according to the method of the invention. System 10 is comprised of an oval-shaped ·member 22 suitably united to a dependent member 13. Member 22 contacts the fundus 23 of uterus 11 and member 22 is made with a release rate controlling wall 20 surrounding an internal reservoir containing progestational steroid, not shown in FIG. 3. System 10 is sized, shaped and adapted for prolonged placement in uterus 11 for releasing progestational steroid for treating hypermenorrhea.

FIG. 4 represents another intrauterine system 10 useful for the controlled and continuous release of progestational agents to uterus 11. System 10 is Y-shaped comprising a pair of members 24 and 25 having a slope corresponding to the triangular slope or uterus 11 with members 24 and 25 integrally united to a descending member 26 that has an axis parallel to the axis of the cervical anal 27. System 10 is made with a release rate controlling wall surrounding an internal reservoir containing progestational steroid, not shown in FIG. 4. System 10 is sized, shaped and adapted for continuous and prolonged placement in uterus 11 for releasing progestational steroid for treating hypermenorrhea.

Other intrauterine devices can be used for the present purpose including one comprised of an elongated body arranged in sinuous form substantially in one plane with imaginary boundaries of an isosceles trapezoid. One such intrauterine device is shaped like a large S continuing into a smaller S as disclosed by Lippes, J., in U.S. Pat. No. 3,250,271.

DETAILED DESCRIPTION OF THE INVENTION

In carrying out the mode and manner of the invention, it has now been unexpectedly discovered that progestational steroids can be administered in low doses to the uterus for the relief of hypermenorrhea. The method of the invention comprises administering at least one, or more than one, progestational steroid or optionally its physiologically active derivative from an intrauterine therapeutic system positioned in the uterus. The system delivers the steroid to the uterus and its surrounding tissues in a controlled and continuous therapeutically effective amount over a prolonged period of time. The progestational steroid is administered according to a precise dosage program. The purpose of the program is to administer the progestational steroid in an amount needed for alleviating hypermenorrhea while simultaneously avoiding introducing the steroid into systemic circulation and saturating the uterine tissues with excess progestational steroid. The amount of progestational steroid administered is an effective amount for relief of hypermenorrhea up to 200 micrograms per hour over a prolonged period of up to 3 years, or longer. In a now preferred embodiment, the amount administered is from 5 nanograms up to 100 micrograms per day over a prolonged period of 1 to 2 years. Generally, the intrauterine system contains an amount sufficient to provide relief from hypermenorrhea over a prolonged period of time, usually about 0.1 mg to 5 g or more of at least one or a mixture of progestational steroids.

In the specification and the accompanying claims the phrase "progestational steroid" broadly includes substances possessing a cyclopentanophenanthrene nucleus of naturally occurring or synthetic origin. The term "steroid" also includes hormones and agents and these terms are considered interchangeable. The term "progestational" as used herein also embraces progestogens and progestins. Progestational agents useful for the purpose of the present invention are represented by the following formula:

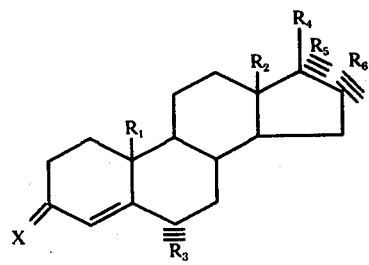

wherein $R_1$, $R_2$ and $R_3$ are independently selected from the group consisting of hydrogen and lower alkyl, $R_4$ is a member selected from the group consisting of hydroxyl and acyl, $R_5$ and $R_6$ are independently selected from the group consisting of hydrogen, hydroxyl and acyloxy, $R_5$ and $R_6$ when taken together is a

group wherein w is a lower alkyl and p is a member selected from the group consisting of lower alkyl and phenyl and x is oxygen or dihydrogen ($H_2$); and a steroid of the formula:

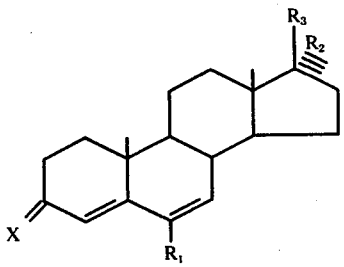

wherein x is a member selected from the group consisting of oxygen and dihydrogen ($H_2$), $R_1$ is a member selected from the group consisting of lower alkyl and halogen, $R_2$ is a member selected from the group consisting of lower alkyl and acyloxy, and $R_3$ is an acyl group; a steroid of the general formula:

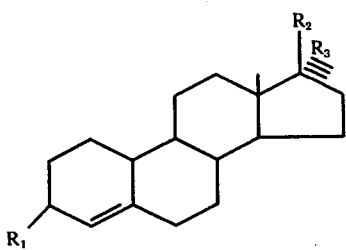

wherein $R_1$ is a member selected from the group consisting of hydroxyl and acyloxy, $R_2$ is a member selected from the group consisting of hydrogen and acyloxy, and $R_3$ is a lower alkynyl group; and a steroid of the formula:

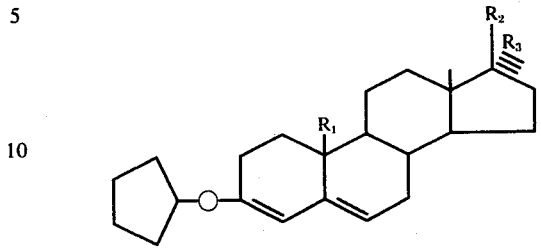

wherein $R_1$ is a member selected from the group consisting of hydrogen and lower alkyl, $R_2$ is a member selected from the group consisting of acyl and acyloxy, and $R_3$ is a member selected from the group consisting of hydroxyl and lower alkynyl.

In the above formula, the term "lower alkyl" embraces straight and branched chain alkyl groups of 1 to 7 carbon atoms, the term "lower alkynyl" includes straight and branched chain groups of 2 to 7 carbon atoms, the term "acyl" embraces acyl groups of 1 to 20 carbons including alkanoyl of 1 to 20 carbon and alkenyl of 2 to 20 carbons, and the term "acyloxy" embraces acyloxy groups of 1 to 20 carbons including alkanoyloxy of 1 to 20 carbons and alkenyloxy groups of 2 to 20 carbons inclusive.

Exemplary steroids possessing progestational activity suitable for the purpose of the invention include the following:

$\Delta^4$-pregnene-3-20-dione also known as progesterone

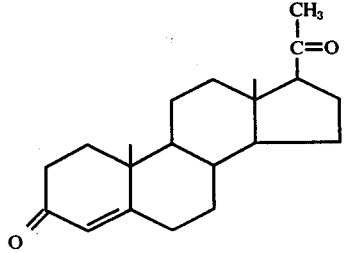

6α-methyl-4-pregen-17α-ol-3,20-dione or medroxyprogesterone

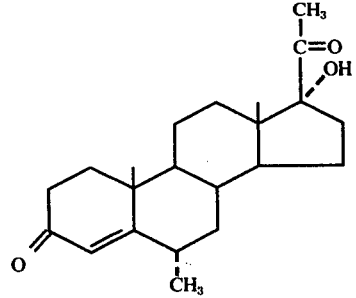

6α-methyl-17α-acetoxyprogesterone or medroxyprogesterone acetate

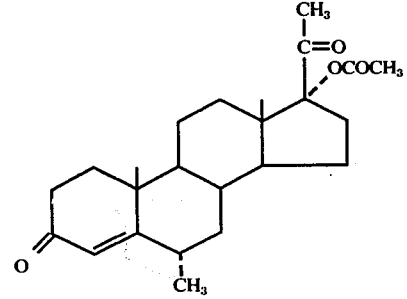

-continued
17α-ethynyl-17β-hydroxy-
4-androsten-3-one, or
ethisterone
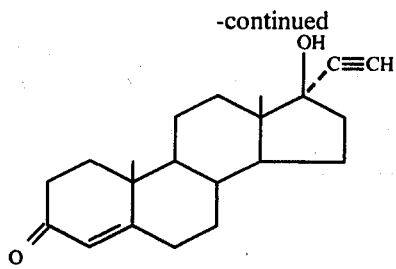
6α-methyl-17-(1-propynyl)-
testerone or dimethisterone
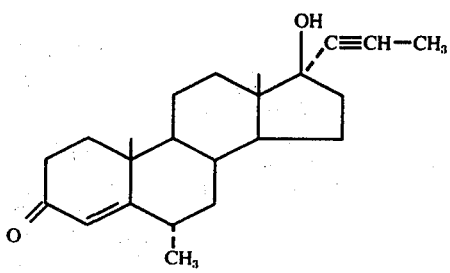
17-hydroxy-19-nor-17α-pregn-
4-en-20-yn-3-one or nor-
ethindrone
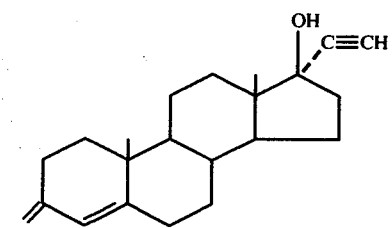
19-nor-17-ethynyl-testosterone
acetate or northindrone acetate
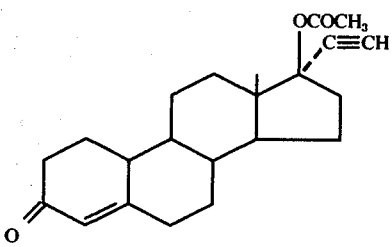
dl-13β-ethyl-17α-ethynyl-17β-
hydroxygon-4-en-3-one or
norgestrel
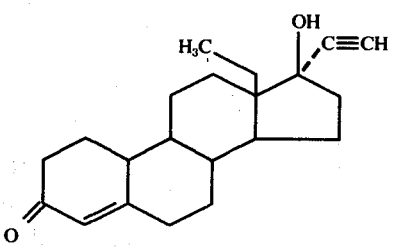
17-hydroxy-19-nor-17α-
pregn-5(10)-en-20-yn-3-one
or norethynodrel
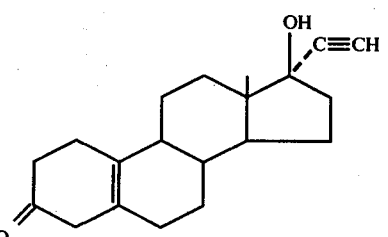
19-nor-17α-pregn-4-en-20-
yne-3β-17-diol or ethynodiol
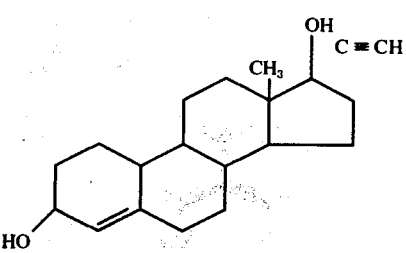

-continued
17α-ethynyl-4-estrene-3β,17β-diol diacetate or ethynodiol diacetate
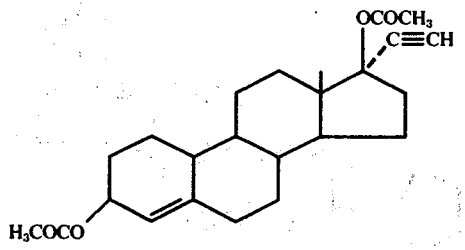
3-(cyclopentyloxy)-19-nor-17α-pregna-3,5-dien-20-yn-17-ol acetate or quingestanol acetate
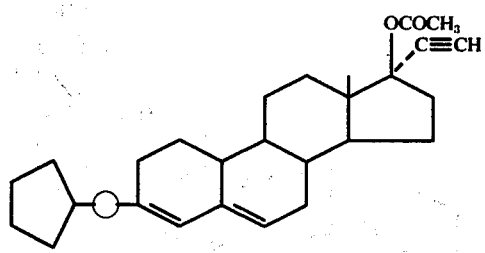
17α-ethynylester-4-en-17β-ol or lynestrenol
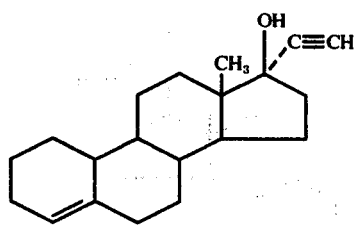
17α-acetoxypregesterone
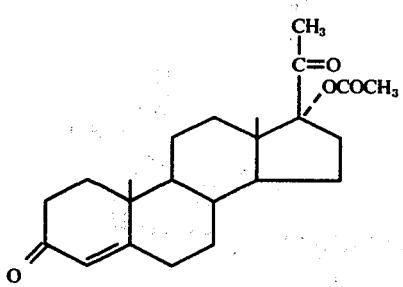
17-hydroxypregn-4-ene-3,20-dione
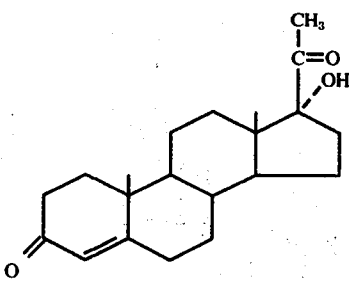
17α-hydroxypregn-4-ene-3,20-dione hexanoate
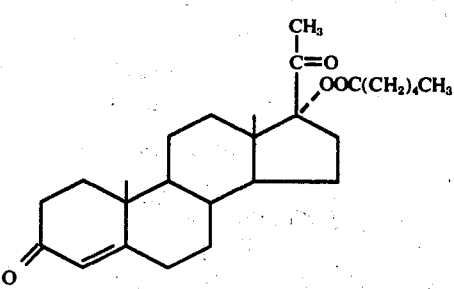

17-hydroxypregesterone-
3-cyclopentyl enol ether
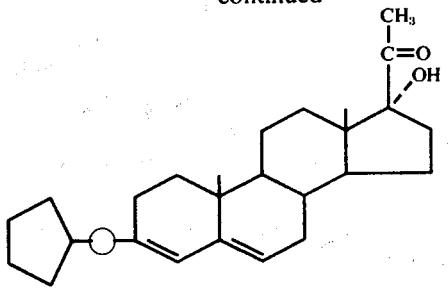
17α-acetoxyprogesterone-
3-cyclopentyl enol ether
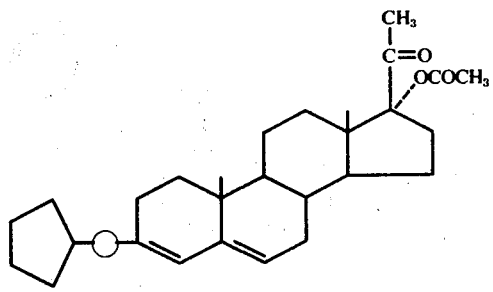
17α-hydroxy-6-methyl-
pregna-4,6-diene-3,20-dione
acetate or megestrol acetate
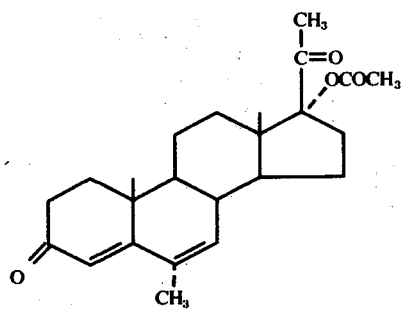
6-chloro-17-hydroxypregna-
4,6-diene-3,20-dione acetate
or chloromadinone acetate
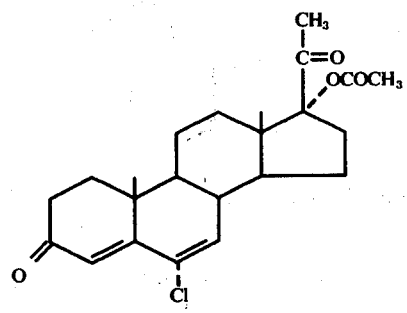
6,17-dimethylpregna-4,6-
3,20-dione or megrogestone
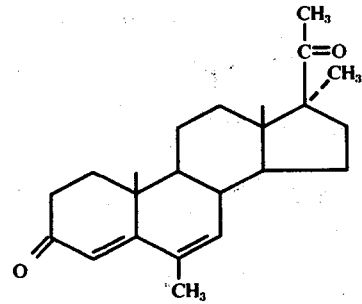
10α-pregna-4,6-dione-3,20-
dione or dydrogesterone
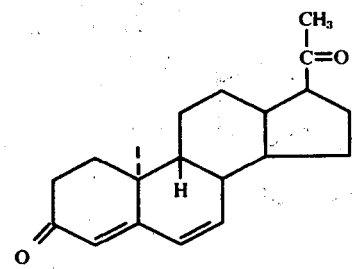

-continued
6-methyl-16-methylene-6-dehydron-17α-acetoxy-progesterone or melengestrol acetate
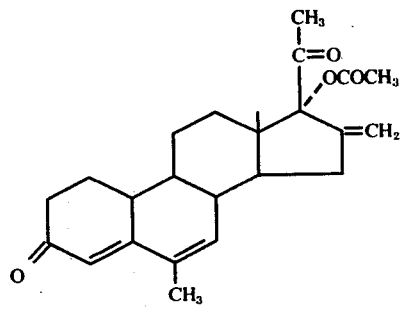
R-16α,17-dihydroxy-pregn-4-ene-3,20-dione cyclic 16,17-acetal-β-methyl-α-phenyl or acetophenide
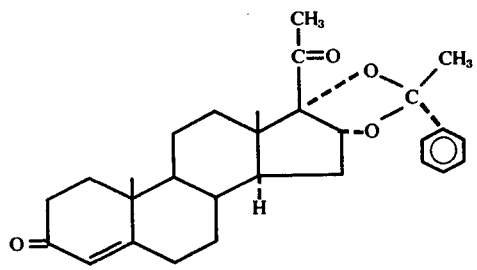
6,16α-dimethyl-6-dehydron 17α-acetoxy-progesterone
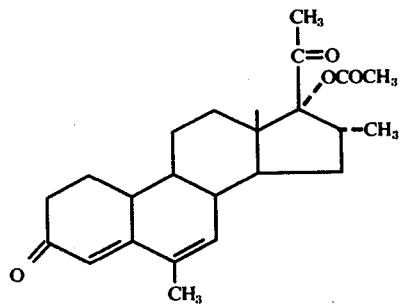
3-(cyclopentyloxy)-pregna-3,5-dien-20-one or quingestrone
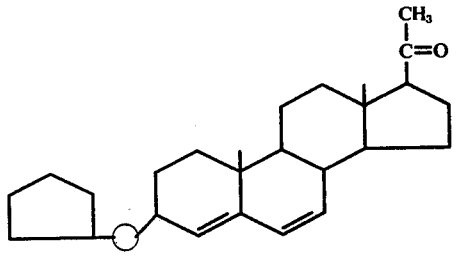
16α,17-dihydroxypregn-4-ene-3,20-dione or alphasone
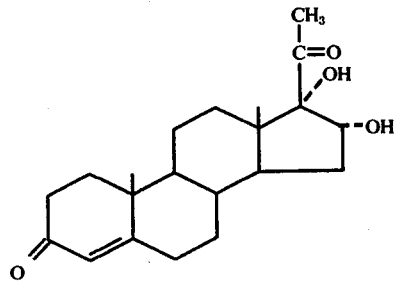
17α-ethynyl-5-estren-17β-ol
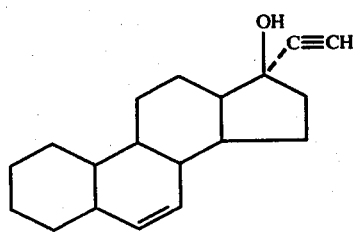

17α-ethynyl-17-hydroxy-estra-
4,9,11-trien-3-one or nor-
gestrienone

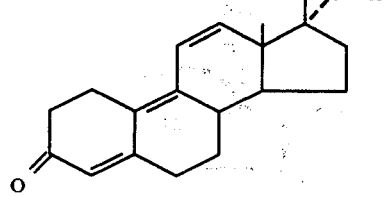

17α-vinyl-estr-5(10)-17β-ol-
3-one or norvindrel

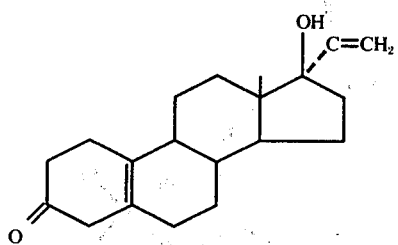

dl-13β-ethyl-17α-ethynyl-17-
hydroxy-gon-4-en-3-one

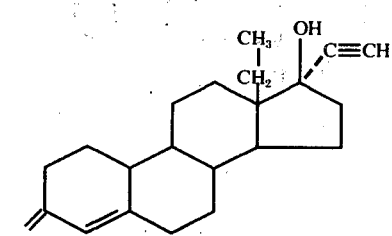

19-nor-3-desoxy-17-allyltestos-
terone or allylestrenol

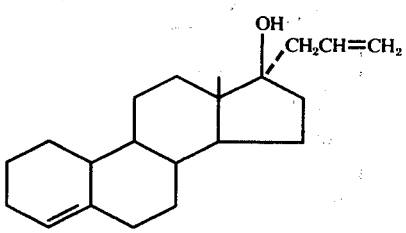

The above steroids are known to the art in U.S. Pat. Nos. 2,379,882; 2,725,389; 2,744,122; 2,753,360; 2,927,119; 3,000,883; 3,000,914; 3,147,290; 3,176,013; and 3,179,675; and in *Ber.*, Vol. 71, page 1024, 1938; *Chem. j Ind.*, page 905, 1959; *J. Am. Chem. Soc.*, Vol. 82, page 746, 1960; *Tetrahedron*, Vol. 19, page 289, 1963; British Pat. No. 870,286; and German Pat. No. 1,075,114.

The above progestational steroids can be used as the pharmacologically acceptable derivatives, such as the derivatives of their hydroxy or keto group. Such derivative should convert to the parent compounds upon release from the intrauterine system by enzymatic transformation, pH assisted hydrolysis and the like. Suitable derivatives include hydrolyzable esters such as formate, acetate, propionate, butyrate, valerate, caproate, hexanoate, heptanoate, caprylate, maleate, citrate, perlargonate, succinate, tartrate, fumarate, malate, ascorbate, sulphate, phosphate, and the like. Of course, the acyl radical of other organic carboxylic acids containing 1 to 20 carbons can be used. These include the residue of hydrocarbon carboxylic acids such as alkanoyl and alkenoyl. These are known to the art in U.S. Pat. Nos. 2,873,271; 3,415,818 and 3,892,842. The last cited patent is assigned to the Alza Corporation of Palo Alto, Calif.

Carriers suitable for use in the reservoir include propylene glycol, silicone oil, glycerin, corn oil, mineral oil, saline and the like. Materials suitable for forming the wall of a reservoir device or for making a device having progestational agent dispersed therethrough include vinylchloride diethylfumarate, poly(dimethyl-siloxane), cross-linked partially hydrolyzed insoluble poly(vinyl alcohol), ethylene vinylacetate copolymer, polyethylene and the like. Examples of other carriers and wall forming materials are described in U.S. Pat. Nos. 3,845,761 and 3,896,819 which patents are assigned to the Alza Corporation of Palo Alto, Calif.

The method of the invention is performed in a presently preferred embodiment by positioning a T-shaped intrauterine therapeutic system containing progesterone in the uterus of a woman afflicated with hypermenorrhea for releasing progesterone thereto. The system presently used administers about 50 to 70 micrograms per day to the uterus over a prolonged period of 1 year. The system is made of ethylene-vinyl acetate copolymer and the reservoir contains progesterone in silicone oil. The system is fully described in U.S. Pat. No. 3,845,761, which patent is herein incorporated by reference and is assigned to the Alza Corporation of Palo Alto, Calif.

Figure 5B:
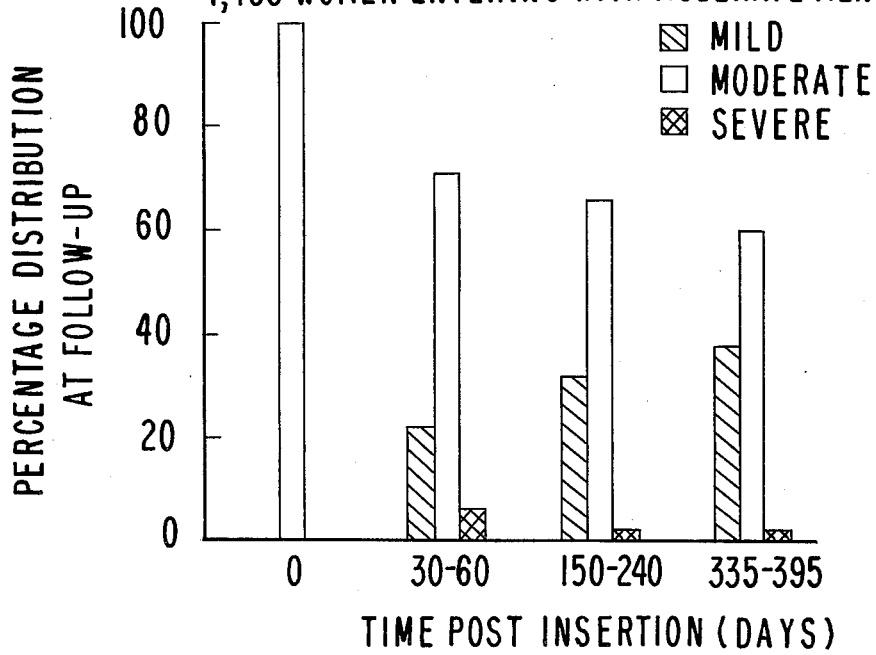

At the time of placement, and at follow-up visits, the women were asked to rate their menstrual flow as mild, moderate or severe. The follow-up visits occurred between 30–60, 150–240 and 335–395 days after placement of the system. The results of controlled and continuous administration of progesterone to the uterus over a prolonged period of time indicated a substantial improvement in the management of hypermenorrhea. The results are illustrated in accompanying FIGS. 5a, 5b and 5c. FIG. 5a represents the results obtained when the system was placed in the uterus of 1,370 women who had a mild menstrual flow at the time the system was positioned in the uterus. FIG. 5b represents the results obtained when the system was placed in the uterus of 4,488 women who had a recent history of moderate menstrual flow at the time of insertion of the system. FIG. 5c illustrates the results for 368 women who reported a recent history of severe hypermenorrhea as indicated by heavy menstrual flow at the time the progestational releasing system was placed in the viable uterus.

It will be understood by those versed in the art in the light of the present specification, drawings and accompanying claims that this invention makes available both a novel and useful method for the management of hypermenorrhea that represents a valuable contribution to the medical art. And, it will be further understood by those versed in the art that many different embodiments of this invention can be made without departing from the scope of the invention. Accordingly, it is to be understood the invention is not to be construed as limited, but it embraces all equivalents inherent therein.

What is claimed is:

1. A method for treating hypermenorrhea in a warm blooded animal which method comprises administering to the uterus of the animal from a means sized, shaped and adapted for placement in the uterus a therapeutically effective amount of a progestational steroid for a prolonged period of time to impart relief from said hypermenorrhea.

2. The method for treating hypermenorrhea according to claim 1 wherein the means is formed of a progestational steroid release rate controlling material that releases a therapeutically effective amount up to 200 micrograms per hour of said steroid over a prolonged period of up to 3 years.

3. The method for treating hypermenorrhea according to claim 1 wherein the progestational steroid is progesterone.

4. The method for treating hypermenorrhea according to claim 1 wherein the progestational steroid is administered from a means in the form of an intrauterine device sized, shaped and adapted for insertion and retention in the uterus with the device having a release rate controlling wall for releasing the steroid from the device to the uterus.

5. The method for treating hypermenorrhea according to claim 4 wherein the device comprises a transverse member and a dependent member united to the transverse member.

6. The method for treating hypermenorrhea according to claim 4 wherein the device is T-shaped and the release rate controlling wall is formed of an ethylene-vinyl acetate copolymer.

7. The method for treating hypermenorrhea according to claim 1 wherein the progestational steroid is administered to the uterus from about 50 to 70 micrograms per day.

8. A method for the management of hypermenorrhea which comprises administering to the uterus of a warm blooded animal having hypermenorrhea a therapeutically effective amount of a progestational hormone having the following formula:

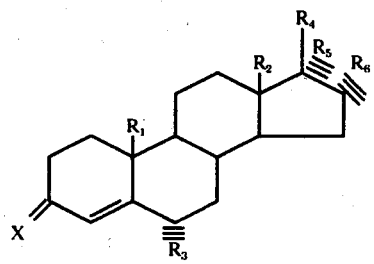

wherein $R_1$, $R_2$ and $R_3$ are independently selected from the group consisting of hydrogen and lower alkyl; $R_4$ is a member selected from the group consisting of hydroxyl and acyl; $R_5$ and $R_6$ are independently selected from the group consisting of hydrogen, hydroxyl and acyloxy; $R_5$ and $R_6$ when taken together consists of a

group wherein w is a lower alkyl and p is a member selected from the group consisting of alkyl and phenyl, and x is a member selected from the group consisting of $H_2$ and oxygen.

9. A method for the management of hypermenorrhea which comprises administering to the uterus of a warm blooded animal having hypermenorrhea an effective amount of a progestational hormone having the following formula:

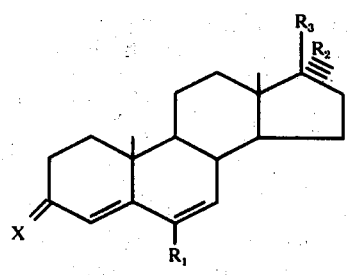

wherein x is a member selected from the group consisting of oxygen and $H_2$; $R_1$ is a member selected from the group consisting of lower alkyl and halogen; $R_2$ is a member selected from the group consisting of lower alkyl and acyloxy; and $R_3$ is an acyl group wherein the hormone when administered to the uterus alleviates hypermenorrhea.

10. A method for alleviating hypermenorrhea comprising administering to the uterus of a warm blooded animal exhibiting hypermenorrhea a therapeutically effective amount of a progestational steroid having the following formula:

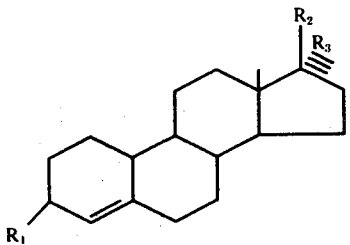

wherein $R_1$ is a member selected from the group consisting of hydroxyl and acyloxy; $R_2$ is a member selected from the group consisting of hydrogen and acyloxy; and $R_3$ is a lower alkynyl, and wherein the hormone when administered to the uterus alleviates hypermenorrhea.

11. A method for alleviating hypermenorrhea comprising administering to a warm blooded animal's uterus a progestational steroid of the following formula:

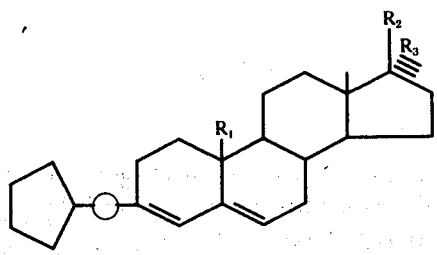

wherein $R_1$ is a member selected from the group consisting of hydrogen and lower alkyl; $R_2$ is a member selected from the group consisting of acyl and acyloxy; and $R_3$ is a member selected from the group consisting of hydroxyl and lower alkynyl, and wherein the steroid is administered in a therapeutically effective amount for alleviating hypermenorrhea in an animal suffering with same.

12. A method for treating hypermenorrhea comprising administering to a woman having hypermenorrhea a progestational steroid selected from the group consisting of $\Delta^4$-pregnene-3-20-dione; 6α-methyl-4-pregnen-17α-ol-3,20-dione; 6α-methyl-17α-acetoxyprogesterone; 17α-ethynyl-17β-hydroxy-4-androsten-3-one; 6α-methyl-17-(1-propynyl)-testerone; 17-hydroxy-19-nor-17α-pregn-4-en-20-yn-3-one; 19-nor-17-ethynyltestosterone acetate; dl-13β-ethyl-17α-ethynyl-17β-hydroxygon-4-en-3-one; 17-hydroxy-19-nor-17α-pregn-5(10)-en-20-yn-3-one; 19-nor-17α-pregn-4-en-20-yne-3β-17-diol; 17α-ethynyl-4-estrene-3β-17β-diol diacetate; 3-(cyclopentyloxy)-19-nor-17α-pregna-3,5-dien-20-yn-17-ol acetate; 17α-ethynylester-4-en-17β-ol; 17α-acetoxyprogesterone; 17-hydroxypregn-4-ene-3,20-dione; 17α-hydroxypregn-4-ene-3,20-dione hexanoate; 17-hydroxypregesterone 3-cyclopentyl enol ether; 17α-acetoxyprogesterone 3-cyclopentyl enol ether; 17α-hydroxy-6-methyl-pregna-4,6-diene-3,20-dione acetate; 6-chloro-17-hydroxypregna-4,6-diene-3,20-dione acetate; 6,17-dimethyl-pregna-4,6-3,20-dione; 10α-pregna-4,6-diene-3,20-dione; 6-methyl-16-methylene-6-dehydro-17α-acetoxy-progesterone; R-16α,17-dihydroxy-pregn-4-ene-3,20-dione cyclic 16,17-acetal β-methyl-α-phenyl; 6,16α-dimethyl-6-dehydro-17α-acetoxy-progesterone: 3-(cyclopentyloxy)-pregna-3,5-dien-20; 16α,17-dihydroxypregn-4-ene-3,20-dione; 17α-ethynyl-5-estren-17β-ol; 17α-ol; 17α-ethynyl-17-hydroxy-estra-4,9,11-trien-3-one; 17α-vinyl estr-5(10)-17β-ol-3-one; dl-13β-ethyl-17α-ethynyl-hydroxy-gon-4-en-3-one; and 19-nor-3-desoxy-17-allyltestosterone, and wherein the progestational steroid is administered to the uterus of said woman from an intrauterine therapeutic system in the form of an intrauterine device in a controlled and continuous therapeutic amount sufficient for relieving hypermenorrhea.

13. A method for treating hypermenorrhea according to claim 12 wherein the intrauterine therapeutic system is 7-shaped.

14. A method for treating hypermenorrhea according to claim 12 wherein the intrauterine therapeutic system is in the shape of a large S continuing into a smaller S.

15. A method for treating hypermenorrhea according to claim 13 wherein the steroid is progesterone.

16. A method for treating hypermenorrhea which method comprises administering from an intrauterine device sized, shaped and adapted for placement in the uterus and formed of a biologically inert polymer containing 0.1 milligrams to 5 grams of progestational steroid, from 5 nanograms to 100 micrograms of the progestational steroid per day over a prolonged period of time to the uterus of a woman having hypermenorrhea to impart relief from same.

17. A method for treating hypermenorrhea which method comprises (a) placing an intrauterine device sized, shaped and adapted for placement and retention in the uterus and formed with an internal reservoir containing from 0.1 milligrams to 5 grams of a progestational steroid and (b) administering from the device from 5 nanograms to 100 micrograms of the progestational steroid per day over a prolonged period of time to the uterus of a woman having hypermenorrhea to impart relief from same.

* * * * *